United States Patent [19]

Aoshima et al.

[11] Patent Number: 4,518,796

[45] Date of Patent: May 21, 1985

[54] METHOD FOR PREPARING CARBOXYLIC ESTERS

[75] Inventors: Atsushi Aoshima, Yokohama; Yoshio Suzuki, Fuji; Setsuo Yamamatsu, Fuji; Tatsuo Yamaguchi, Fuji, all of Japan

[73] Assignee: Asahi Kasei Kogyo Kabushiki Kaisha, Osaka, Japan

[21] Appl. No.: 149,387

[22] Filed: May 13, 1980

[30] Foreign Application Priority Data

| May 17, 1979 [JP] | Japan | 54-59631 |
| May 17, 1979 [JP] | Japan | 54-59632 |
| May 17, 1979 [JP] | Japan | 54-59634 |

[51] Int. Cl.$^3$ ............................................. C07C 67/39
[52] U.S. Cl. .................................... 560/208; 560/77; 560/103; 560/106; 560/112; 560/113; 560/190; 560/193; 560/198; 560/201; 560/238
[58] Field of Search ................ 560/208, 238, 77, 103, 560/106, 112, 113, 190, 193, 198, 201; 562/531

[56] References Cited

U.S. PATENT DOCUMENTS

| 3,639,449 | 2/1972 | Kunugi et al. | 560/238 |
| 3,655,747 | 4/1972 | Sennewald et al. | 562/531 |
| 3,772,381 | 11/1973 | Nakamura et al. | 560/208 |

OTHER PUBLICATIONS

Emel'yanov, B. V. et al., *Chemical Abstracts*, vol. 54, (1960), #7003b.

*Primary Examiner*—Natalie Trousof
*Assistant Examiner*—L. Hendriksen
*Attorney, Agent, or Firm*—Sprung Horn Kramer & Woods

[57] ABSTRACT

A method for preparing a carboxylic ester by reacting an aldehyde with an alcohol in the presence of oxygen with a catalyst, characterized in that the catalyst is a solid catalyst comprising palladium and bismuth, which may form an intermetallic compound, and which catalyst may comprise an alkali metal compound or an alkaline earth metal compound. The aforesaid catalyst avoids decomposition reactions simultaneously with the desired reaction, and therefore, the desired compound can be obtained in a high yield.

11 Claims, No Drawings

METHOD FOR PREPARING CARBOXYLIC ESTERS

This invention relates to a method for preparing a carboxylic ester, and more particularly, to a method for preparing a carboxylic ester by bringing an aldehyde and an alcohol into contact with a specific catalyst in the presence of oxygen.

There has hitherto been known a method for preparing carboxylic esters comprising suspending a catalyst in which palladium metal is supported on a carrier such as silica, alumina, diatomaceous earth, active carbon or the like, in a mixture of an aldehyde and an alcohol and blowing a molecular oxygen-containing gas thereinto under pressure to oxidize the aldehyde in the liquid phase and simultaneously esterifying the same (see, for example, Japanese Patent Publication No. 34368/70). However, this method has the disadvantages that the starting aldehyde and its oxidation intermediate are decomposed to violently generate carbon dioxide and hydrocarbons, thereby decreasing the yield of the objective carboxylic ester, and that since the starting alcohol per se is oxidized to form the corresponding aldehyde, which reacts in turn with the starting alcohol to form an undesirable carboxylic ester (for example, when ethanol is used as the alcohol, ethyl acetate is formed), the selectivity for the objective compound, particularly the selectivity based on the alcohol, is greatly decreased.

In order to inhibit the formation of carboxylic esters from an alcohol and an aldehyde corresponding to the alcohol and the decomposition of the starting aldehyde, the present inventors have conducted extensive research, and it has consequently been discovered that the abovementioned purpose can be achieved by use of a solid catalyst comprising palladium and bismuth, and optionally an alkali metal compound or alkaline earth metal compound in the reaction of an aldehyde with an alcohol in the presence of oxygen, whereby the desired carboxylic ester can be prepared with a high selectivity.

According to this invention, there is provided a method for preparing a carboxylic ester by reacting an aldehyde with an alcohol in the presence of oxygen with a catalyst, characterized in that the catalyst is a solid catalyst comprising palladium and bismuth, and optionally an alkali metal compound or an alkaline earth metal compound.

When methacrolein is used as the aldehyde and methanol as the alcohol, the reaction path in the production for a carboxylic ester according to this invention can be indicated by the following reaction formulas:

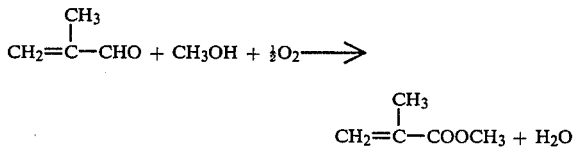

As the aldehyde used in this invention, there may be mentioned, for example, saturated aliphatic aldehydes such as formaldehyde, acetaldehyde, propionaldehyde, isobutyraldehyde, glyoxal and the like; $\alpha,\beta$-unsaturated aliphatic aldehydes such as acrolein, methacrolein, crotonaldehyde and the like; aromatic aldehydes such as benzaldehyde, tolualdehyde, benzylaldehyde, phthalaldehyde and the like; and derivatives of these aldehydes. These aldehydes may be used alone or in admixture of two or more. Further, as the aldehyde source there may be used a compound which gives an aldehyde in the reaction system such as a primary alcohol, because the primary alcohol is also oxidized with the present catalyst to the corresponding aldehyde. However, since the present catalyst catalyzes preferentially the reaction of an aldehyde with an alcohol, the presence of the aldehyde inhibits the oxidation of the alcohol, whereby the production of diverse carboxylic esters as by-products is inhibited. When no aldehyde is used, the primary alcohol is oxidized to the corresponding aldehyde and the aldehyde thus produced reacts with the alcohol rapidly to give the corresponding carboxylic ester, and therefore primary alcohols may be used as the aldehyde source.

As the alcohol used in this invention, there may be mentioned, for example, saturated aliphatic alcohols such as methanol, ethanol, isopropanol, octanol and the like; diols such as ethylene glycol, butanediol and the like; unsaturated aliphatic alcohols such as allyl alcohol, methallyl alcohol and the like; aromatic alcohols such as benzyl alcohol and the like. In particular, lower alcohols such as methanol, ethanol and the like react rapidly and hence are preferred. These alcohols may be used alone or in admixture of two or more.

The ratio of the amount of the aldehyde used to the amount of the alcohol used in the reaction of this invention is not particularly limited, and the reaction may be effected over a wide range of aldehyde to alcohol molar ratio such as 10/1 to 1/1000, though, in general, the amount of the aldehyde is preferably small, for example, the aforesaid ratio ranges preferably from ½ to 1/50.

The oxygen used in this invention is molecular oxygen, and may be either oxygen gas itself or a mixed gas prepared by diluting oxygen gas with a diluent inert to the reaction, for example, nitrogen, carbon dioxide or the like, and air may also be used. The quantity of oxygen present in the reaction system is not less than the stoichiometric quantity required for the reaction, preferably not less than 1.2 times the stoichiometric quantity.

It is essential that the catalyst used in the process of this invention comprises both palladium and bismuth, and it is preferably that the palladium is in the reduced state, namely of zero valency, and not in the cationic state, and the bismuth is present as metallic bismuth or bismuth compounds, and the two elements are present in the reaction system in such a form that the two can have some interaction with each other. Palladium and bismuth may preferably form an alloy, an intermetallic compound or the like.

The catalyst may contain other elements such as Te, Cr, Co, Cd, In, Ta, Cu, Zr, Hf, W, Mn, Ag, Re, Sb, Sn, Rh, Ru, Ir, Pt, Ni, Au, Ti, Al, B and the like.

These catalyst constituents may be used in the state that they are supported on a general carrier such as active carbon, silica, alumina, or the like, or a special carrier such as magnesia, titania, calcium carbonate, or the like, and the amount of the metallic constituents supported on a carrier may be usually 0.1 to 20% by weight, preferably 1 to 10% by weight, based on the weight of the carrier though it is not critical. The catalyst constituents may also be used in the metallic form or in the form of compounds without supporting them on a carrier. The ratio of palladium to bismuth in the catalyst is preferably 1:0.05–10 (atomic ratio) for achieving the above-mentioned purpose.

The amount of the catalyst used may be varied freely depending on the kind and amount of the starting materials, the method of preparing the catalyst, operation conditions and the like, though the catalyst is generally used in a weight ratio to the starting aldehyde of about 1/1000-20/1. However, as mentioned above, the catalyst may be used in an amount outside this range. In particular, it is the matter of course that the amount of the catalyst is not restricted to said range in the case of flow system reaction.

According to another embodiment of the method of this invention, a catalyst comprising palladium, bismuth and an alkali metal compound or alkaline earth metal compound is used. Although it is not clear in what state said alkali metal compound or alkaline earth metal compound is present, the incorporation of said alkali metal compound or alkaline earth metal compound into the catalyst brings about a remarkable effect on improvement in the activity and selectivity of the catalyst. Particularly preferable are compounds of alkaline earth metals such as magnesium, calcium and the like. These alkali metal compounds or alkaline earth metal compounds may be used alone or in combination of two or more.

The catalyst can be prepared in a conventional manner. For example, a soluble salt such as palladium chloride can be reduced with a reducing agent such as formalin in aqueous solution to deposit metallic palladium and the deposited metallic palladium is filtered to prepare a metallic palladium catalyst, or a suitable carrier can be impregnated with an aqueous acidic solution of a soluble palladium salt and the impregnated carrier is subjected to reduction with a reducing agent to prepare a supported palladium catalyst. When it is intended to prepare a catalyst in which palladium and a bismuth compound are supported on a carrier, a suitable carrier is impregnated with an aqueous solution of a soluble palladium salt, and the impregnated carrier is reduced with a suitable reducing agent, after which the reduced carrier is immersed in an aqueous solution of bismuth nitrate, evaporated to dryness and dried. Alternatively, the catalyst may be prepared by first supporting the bismuth compound on the carrier, then impregnating the carrier with the palladium salt, and thereafter reducing the palladium salt.

As the bismuth compound used in the preparation of the above catalyst, any bismuth-containing compound may be used, though fatty acid salts of bismuth, for example, bismuth acetate, bismuth stearate, and the like; bismuth oxide; bismuth hydroxide; bismuth nitrate are preferably used. These bismuth compounds may be anhydrous or may contain crystal water.

The reaction of this invention may be effected at a temperature of 0° to 100° C., though a temperature as low as 20° to 80° C. is preferred. Though the reaction may be effected under reduced pressure, at atmospheric pressure, or under pressure, it is possible to produce the desired carboxylic ester with a high yield by a very simple method of blowing oxygen or an oxygen-containing gas into the reaction system at normal pressure. This is a characteristic feature of this invention. The reaction may be carried out batchwise or continuously.

When the method of this invention is carried out by the liquid phase reaction or by trickle flow reaction, it is preferable to add an alkali metal compound or an alkaline earth metal compound, for example, an oxide, a hydroxide, a carbonate or the like to maintain the pH of the reaction system at 6 to 8. As the pH of the reaction system exceeds 8, the side reaction of the starting aldehyde becomes violent, and the selectivity for the desired carboxylic ester tends to be reduced. On the other hand, as the pH of the reaction system becomes less than 6, the maintenance of the catalyst activity tends to be adversely affected.

This invention is explained below referring to Examples, but the Examples are by way of illustration and not by way of limitation. In the Examples, "%" is by weight unless otherwise specified.

EXAMPLE 1

To diluted aqueous hydrochloric acid containing 0.83 g of palladium chloride was added 10 g of coconut husk active carbon, and the mixture was subjected to hot impregnation at 60° C. To the mixture were added 2 ml of aqueous formaldehyde solution and 1N aqueous sodium hydroxide solution. The supported catalyst thus obtained was separated by filtration, washed with water and dried. Bismuth oxide was supported thereon in a proportion of 1% in terms of metallic bismuth to prepare a catalyst.

In a 200-ml four-necked flask equipped with a dry ice-methanol condenser, a gas-inlet, a stirrer and a thermometer were placed 100 ml of methanol, 4 g of the above catalyst and 3.5 g of methacrolein, and the mixture was subjected to reaction at 40° C. for 2 hrs while passing air therethrough at a rate of 10 liters/hr. After the lapse of 2 hrs, the conversion of methacrolein was 72%, the yield of methyl methacrylate was 52.9% (selectivity 73.5%), and a small amount of methyl formate (0.4 g), propylene (selectivity 3.2%) and carbon dioxide were produced as by-products.

EXAMPLE 2

In 40 ml of water was dissolved 1.76 g of magnesium acetate [$(CH_3COO)_2Mg.4H_2O$], and 10 g of silica gel (Fuji Davidson 5D) was added thereto, impregnated with the solution and evaporated to dryness with stirring on a boiling-water bath, and calcinated in air at 500° C. for 3 hrs, added to diluted aqueous hydrochloric acid containing 0.83 g of palladium chloride heated to 60° C., and then impregnated with the palladium chloride with stirring. After the addition of 2 ml of an aqueous formaldehyde solution and 1N aqueous sodium hydroxide solution, the resulting supported catalyst was separated by filtration, washed with water and dried. Furthermore, bismuth nitrate was supported thereon in a proportion of 0.5% in terms of metallic bismuth. Reaction was effected in the same manner as in Example 1, except that 4 g of the above catalyst was substituted for the catalyst in Example 1. The conversion of methacrolein was 84%, and the yield of methyl methacrylate was 63% (selectivity 75%). The amount of by-products was small.

EXAMPLE 3

Reaction was effected in the same manner as in Example 1, except that 4 g of a catalyst in which bismuth nitrate was supported in an amount of 0.5% in terms of metallic bismuth on a commercially available palladium-carbon (manufactured by Japan Engelhard Co.) was substituted for the catalyst in Example 1, to obtain the result that the conversion of methacrolein was 67%, and the yield of methyl methacrylate was 48.5% (selectivity 72.4%).

EXAMPLE 4

Reaction was effected in the same manner as in Example 1, except that 3.5 g of isobutyraldehyde was substituted for the methacrolein to obtain the result that the conversion of isobutyraldehyde was 68% and the yield of methyl isobutyrate was 59.5% (selectivity 87.5%).

EXAMPLE 5

Reaction was effected in the same manner as in Example 2, except that 5.3 g of benzaldehyde was substituted for the methacrolein, to obtain the result that the conversion of benzaldehyde was 70% and the yield of methyl benzoate was 57% (selectivity 81.4%).

Comparative Example 1

A palladium-supporting catalyst was prepared in the same manner as in Example 1, except that bismuth oxide was not used. Reaction was effected in the same manner as in Example 1, except that 4 g of the above catalyst was substituted for the catalyst in Example 1, to obtain the result that the conversion of methacrolein was 61.5%, the yield of methyl methacrylate was 24.6% (selectivity 40%), and considerable amounts of carbon dioxide and propylene (selectivity 26%) were formed. Methyl formate was also formed in an amount of 1.8 g.

EXAMPLE 6

In diluted hydrochloric acid solution were dissolved 1.76 g of magnesium acetate and 0.56 g of bismuth oxide, and to the solution was added 10 g of silica gel (Fuji Davidson 5D). The resulting mixture was subjected to impregnation and evaporation to dryness on a boiling-water bath while stirring the mixture, and then calcinated in air at 500° C. for 3 hrs. The supported silica gel obtained was added to diluted hydrochloric acid containing 0.83 g of palladium chloride heated to 60° C., and the resulting mixture was then subjected to impregnation with palladium with stirring. Thereafter, 2 ml of aqueous formaldehyde solution and 1N aqueous sodium hydroxide solution were added thereto, and the resulting supported catalyst was separated by filtration, washed with water and dried. This catalyst was subjected to X-ray diffraction using CuKα ray to find that peaks appeared at an angle of diffraction (2 θ) of 38.9°, 45.2°, 65.8° and 79°.

In the same manner as in Example 1, 4 g of the above catalyst, 100 ml of methanol, and 3.5 g of methallyl alcohol was subjected to reaction to obtain the result that the conversion of methallyl alcohol was 100%, the yield of methacrolein was 10.2%, the yield of methyl methacrylate was 72.9% and the yield of methacrylic acid was 3.5%. The amount of propylene and carbon dioxide produced as by-products was small.

EXAMPLE 7

In the same reactor as in Example 1 were placed 4 g of the catalyst of Example 6 and 50 ml of n-propanol, and they were subjected to reaction at 40° C. for 2 hrs while passing air therethrough at a rate of 10 liters/hr, to obtain 0.57 g of propionaldehyde, 4.8 g of propyl pripionate, and 1.18 g of propionic acid. Ethane was also formed in an amount of 1 millimole.

Comparative Example 2

Using a catalyst prepared in the same manner as in Example 6, except that the bismuth oxide was not used, reaction was effected in the same manner as in Example 7, to obtain 0.6 g of propionaldehyde, 3.37 g of propyl propionate and 1.85 g of propionic acid. The amount of ethane formed was 7 millimoles.

EXAMPLE 8

In the same manner as in Example 6, a catalyst in which 2% of magnesium, 2.5% of bismuth and 2.5% of palladium were supported on silica gel was prepared, and then subjected to X-ray diffraction to find that the diffraction peaks thereof were the same as in Example 6. In the same manner as in Example 1, 4 g of the above catalyst, 7 g of methacrolein and 100 ml of methanol were subjected to reaction to obtain the result that the conversion of methacrolein was 86.4%, and the yield of methyl methacrylate was 75.2% (selectivity 87%).

What is claimed is:

1. A method for producing a carboxylic ester comprising reacting an aldehyde with alcohol at 0° to 100° C. in the presence of oxygen and a solid catalyst comprising palladium and bismuth.

2. A method according to claim 1, wherein the solid catalyst comprises an intermetallic compound of palladium and bismuth.

3. A method according to claim 1 or 2, wherein the aldehyde is methacrolein, acrolein or a mixture of them.

4. A method according to claim 1, 2 or 3, wherein the alcohol is methanol, ethanol or a mixture of them.

5. A method according to claim 1 or 2, wherein the solid catalyst comprises as a carrier one member selected from the group consisting of alumina, silica, calcium carbonate, active carbon, magnesium oxide, magnesium hydroxide and an organic high polymer porous material.

6. A method for producing a carboxylic ester by reacting an aldehyde with an alcohol in the presence of oxygen with a catalyst, characterized in that the said catalyst is a solid catalyst comprising (i) palladium, (ii) bismuth and (iii) at least one compound selected from the group consisting of alkali metal compounds and alkaline earth metal compounds.

7. A method according to claim 6, wherein the said catalyst is a solid catalyst comprising (i) an intermetallic compound of palladium and bismuth, and (ii) at least one compound selected from the group consisting of alkali metal compounds and alkaline earth metal compounds.

8. A method according to claim 6, wherein the alkali metal compound and alkaline earth compound are selected from the group consisting of compounds of sodium, potassium, calcium and magnesium.

9. A method according to claim 6, 7 or 8, wherein the said aldehyde is methacrolein, acrolein or a mixture of them.

10. A method according to claim 6, 7 or 8, wherein the aforesaid alcohol is methanol, ethanol or a mixture of them.

11. A method according to claim 6, 7 or 8, wherein the aforesaid catalyst comprises as a carrier one member selected from the group consisting of alumina, silica, calcium carbonate, active carbon, magnesium oxide, magnesium hydroxide and an organic high polymer porous material.

* * * * *